United States Patent [19]
Korb et al.

[11] Patent Number: 5,371,108
[45] Date of Patent: Dec. 6, 1994

[54] DRY EYE TREATMENT PROCESS AND SOLUTION

[75] Inventors: Donald R. Korb, Boston, Mass.; Thomas Glonek, Oak Park, Ill.

[73] Assignee: Ocular Research of Boston, Inc., Boston, Mass.

[21] Appl. No.: 31,645

[22] Filed: Mar. 15, 1993

Related U.S. Application Data

[63] Continuation-in-part of Ser. No. 769,679, Oct. 2, 1991, abandoned.

[51] Int. Cl.$^5$ .................. A61K 31/01; A61K 47/00
[52] U.S. Cl. ................... 514/762; 514/787; 514/912
[58] Field of Search ............. 514/787, 762, 912

[56] References Cited

U.S. PATENT DOCUMENTS

| | | | |
|---|---|---|---|
| 4,522,803 | 6/1985 | Lenk et al. | 424/1.1 |
| 4,861,760 | 8/1989 | Mazuel et al. | 514/54 |
| 4,866,049 | 9/1989 | Maumenee et al. | 514/169 |
| 4,914,088 | 4/1990 | Glonek et al. | 514/76 |

FOREIGN PATENT DOCUMENTS

| | | |
|---|---|---|
| 16149 | 1/1978 | Australia . |
| 0459148A2 | 12/1991 | European Pat. Off. . |

OTHER PUBLICATIONS

"Federal Register", Department of Health and Human Services, Food and Drug Administration, vol. 53, No. 43, Mar. 4, 1988, pp. 7076–7093.

*Primary Examiner*—Zohreh Fay
*Attorney, Agent, or Firm*—Robert L. Goldberg

[57] ABSTRACT

A method and composition for reducing evaporation of an aqueous layer from the surface of the eye. The method comprises applying a gel of oil and wax over the eye, preferably in the form of a meta-stable oil in water emulsion in a dosage not exceeding 100 microliters. The gel is formed by gelling a hydrocarbon oil with a wax, preferably dispersed in aqueous medium at a pH of at least about 8.0.

60 Claims, No Drawings

DRY EYE TREATMENT PROCESS AND SOLUTION

CROSS REFERENCE TO RELATED APPLICATION

This application is a continuation in part of U.S. patent application Ser. No. 07/769,679 filed Oct. 2, 1991, now abandoned.

BACKGROUND OF THE INVENTION

I. Introduction

This invention relates to wetting the surface of the eye and/or an ocular prosthesis, providing mechanical lubrication therefor, reducing the evaporation of fluid from the surface of the eye and delivering a medicament to the ocular surface. In a preferred embodiment of the invention, the invention relates to an ophthalmic composition for dry eye treatment.

II. Description of the Prior Art

It is known that an aqueous tear film extends over the ocular surfaces and maintains the ocular surface moist and lubricated. It is also known that dehydration of moisture from the eye may result in discomfort. Further, it is known that compositions are available in the market intended for dry eye treatment. These compositions are primarily aqueous materials that supplement the tear film.

The most common treatment for dry eye involves temporary alleviation of dry eye symptoms by topical application of a tear substitute that adds a large volume of liquid to the anterior surface of the eye and related adnexa. Typical tear substitute compositions comprise water soluble polymer solutions. Examples of such solutions include saline solutions of polyvinyl alcohol, hydroxypropylmethyl cellulose or carboxymethyl celluloses. U.S. Pat. No. 4,421,748 teaches an artificial tear composition comprising an aqueous hypotonic solution of lecithin and a viscosity adjusting agent such as a solution soluble cellulose.

Methods used to quantify the effectiveness of tear substitutes for dry eye treatment solutions have not been standardized, and many methods used to quantify the results obtained using such tear substitute compositions are often inaccurate. For this reason, it is known that reported relief of dry eye symptoms using known tear substitutes varies considerably from subject to subject, and regardless of the method used to quantify relief using a tear substitute, relief often does not exceed several minutes.

The symptoms associated with dry eye are often exacerbated with subjects using ocular prostheses such as contact lenses. In some cases, contact lens intolerance is caused by the condition of dry eye and its symptoms. Further, the rate of evaporation from the eye is accelerated by the nature of the contact lens surface, and the physical presence of the contact lens results in menisci formation with additional physical and evaporative effects, even with subjects having an adequate tear film. For many subjects, contact lens intolerance is not overcome by topical application of tear substitutes. Therefore, there is a continuing need for improved compositions and processes for treatment of the dry eye condition and for improving tolerance to ocular prostheses.

An improved composition for dry eye treatment is the subject of U.S. Pat. No. 4,914,088 incorporated herein by reference. This patent teaches the use of charged phospholipids for the treatment of dry eye symptoms. In accordance with the patent, a phospholipid composition, preferably in the form of an aqueous emulsion, is topically applied to the eye where it is believed to disperse over the ocular surface and form a film that replicates a lipid layer formed by spreading a naturally occurring lipid secreted principally from the Meibomian glands during blinking. Because the phospholipid, when applied to the eye, carries a net charge, it is believed that aligned molecules repel each other preventing complex aggregate formation thereby resulting in a stable phospholipid film.

In copending U.S. patent applications Ser. Nos. 07/529,657 and 07/638,215, filed respectively May 29, 1990 and Jan. 7, 1991, assigned to the same assignee as the subject application (hereafter the "copending applications") and incorporated herein by reference, further improvements in dry eye treatment are disclosed. In accordance with the disclosures of the copending applications, the dry eye treatment composition of U.S. Pat. No. 4,914,088 is improved by use of an essentially nonpolar oil as a component of a dry eye treatment composition. The oil increases the longevity of the tear film formed on the eye following addition of the dry eye treatment solution, presumably by providing and/or thickening the dehydration barrier (the layer) on the outer surface of the tear film. Thus, the oil increases the efficacy of the dry eye treatment solution and reduces performance variability from subject to subject. In addition, it is a further discovery of the copending applications that for many patients, the use of oil alone is efficacious in treatment of the dry eye condition.

The copending applications also teach the desirability of regulating the dosage of the oil applied to the eye. In accordance with the inventions disclosed in the copending applications, the total amount of oil available for formation of a film does not exceed that amount that would cause blurring and preferably does not exceed 25 ul. As the amount of oil exceeds a desired amount, the oil film formed over the eye becomes excessively thick or, alternatively, oil globules may form on the surface of the eye and not spread evenly over the eye. In either case, a thick oil layer is likely to contribute to patient blurring. The amount of oil beyond which blurring will occur varies from patient to patient and is dependent upon the specific oil used.

To understand how the treatment compositions of the above cited patent and copending applications function, and how the compositions disclosed herein function, the mechanism by which a barrier film over the eye is capable of alleviating dry eye symptoms should be understood.

It is reported that a naturally occurring tear film comprises a complex coating with three separate layers. The inner layer in contact with the ocular surface of the eye is said to be composed primarily of mucous, and renders the hydrophobic epithelial cell plasma membrane surface hydrophilic. The middle layer of the tear film is an aqueous layer. This layer is the thickest portion of the tear film, which is a source of moisture and lubrication for the eye and functions as an optical planarizing layer. The outer layer of the tear film, at the interface with the atmosphere, is a non-polar oily, naturally occurring lipid layer. This oily lipid layer is reported to act as a barrier that prevents evaporation of the aqueous layer (Mishima and Maurice: "The oily layer of the tear film and evaporation from the corneal surface," *Exp. Eye Res.* 1961; 1:39–45). Finally, the oily layer is bound to the aqueous layer through a polar interfacial lipid layer containing phospholipids.

The polar lipids which include the phospholipids, and the non-polar oily lipid components of the tear film are thought to originate primarily from secretions of the Meibomian glands. The oily layer of the tear film is formed from these secretions and is constantly replenished during blinking by expression of the secretions from the Meibomian glands and then spreading of the same over the surface of the eye by the eyelids. By constantly spreading the polar and non-polar lipids over the eye during blinking, the tear film is maintained and evaporation of the aqueous middle layer of the tear film is minimized.

A cause of dry eye is believed to be a deficiency in the quantity or quality of secretions from the Meibomian glands. It is postulated that a cause of dry eye is a deficiency in the polar lipid layer of the tear film, the non-polar oily lipid layer, or both. Regardless of the cause of the deficiency, the compromised lipid layer fails to act as an adequate barrier against evaporation of the aqueous portion of the tear film resulting in one form of the dry eye condition.

In accordance with the invention of U.S. Pat. No. 4,914,088, a charged phospholipid added to the eye is believed to disperse over the ocular surface to form a film replicating the lipid layer formed by spreading a naturally occurring lipid secreted from the Meibomian glands during blinking. Where the phospholipid applied to the eye carries a net charge, it is believed that the aligned molecules repel each other such that complex aggregate formation is prevented and the integrity of the phospholipid film is maintained.

The above-referenced copending applications involve adding a non-polar oil to the eye alone or in combination with the charged phospholipid, preferably in the form of an oil-in-water emulsion. Upon application of the treatment composition to the eye, it was postulated that the negatively charged phospholipid layer forms an aligned film over the aqueous tear film with charged ends dissolved in the aqueous layer and hydrophobic ends furthest removed from the aqueous layer available to bond with the non-polar oil layer. This causes the oil layer to disperse over the top surface of the eye as a thin, continuous and stable layer that functions as an evaporation barrier. Recognizing that the tear film naturally occurring in the eye may be deficient in the phospholipid component, the oil component, or both, the preferred embodiment of the treatment composition of said applications replenished both components of the tear film, thereby reducing variations in efficacy from patient to patient.

In the second of the copending applications, it is disclosed that to avoid blurred vision, the total amount of oil comprising the film over the ocular surface had to be controlled, the treatment composition is desirably added to the eye in the form of a meta-stable emulsion to enhance differentiation of the emulsion on the ocular surface, and the treatment composition desirably contains a surfactant that permits an increase in the oil content of an emulsion enabling rapid formation of a film of the efficacious components of the treatment composition over the ocular surface.

The use of the dry eye treatment of the referenced patent and copending applications assist in overcoming dry eye symptoms as reported therein. However, with time, the thick oil film formed using the compositions of the copending applications thins and dissipates and consequently, there is a continuing need to prolong the presence of the replicated tear film on the ocular surface beyond that disclosed in the copending applications.

SUMMARY OF THE INVENTION

The invention disclosed herein is a further improvement over the inventions disclosed in the above-referenced copending applications. In accordance with this invention, it has been found that the residence time of the oil layer on the eye formed by the procedures disclosed in the copending applications can be further prolonged if a wax is present in the treatment composition, preferably at least partially dissolved with the oil to form a composition having the appearance of a gel. Dissolution or gelation of the wax with the oil may be readily accomplished by blending the oil with a wax at a temperature above the melting point of the wax, preferably in the presence of alkali, and then permitting the mixture to cool. By addition of the solution of the oil and wax to the eye, a replicated tear film will form on the ocular surface of the eye which is believed to be strengthened and better organized over the ocular surface. Accordingly, the residence time of the oil layer on the ocular surface is significantly prolonged. Moreover, and unexpectedly, the layer appears to contribute to blur reduction and thereby is believed to permit somewhat larger doses of treatment composition to be applied to the eye.

Based upon the above, the invention comprises treatment of the eye with a composition that is a sterile solution or gel of oil and wax free of additives pharmaceutically unacceptable to the eye and preferably formed from a non-polar oil and a wax in the presence of a strong alkali in amounts and in a form that avoids blurring while extending the residence time of an artificially formed tear film on the eye. The invention also comprises methods for making the oil and wax gel in a form suitable for use as an eye treatment composition. The treatment composition of the invention is especially useful for the treatment of dry eye symptoms, lubricating an ocular prosthesis and delivering a medicament to the eye over a prolonged period of time.

DESCRIPTION OF THE PREFERRED EMBODIMENTS

The term "solution" and "gel" as used herein refer to a mixture of an oil and wax formed by heating the same together at a temperature in excess of the melting point of the wax. Though not wishing to be bound by theory, it is believed that all or a major portion of the wax dissolves in the oil when following the procedures of the invention though it is possible that some fraction of the wax is present in a treatment composition as a discrete phase as will be described in greater detail below.

The term "treatment composition" as used herein refers to the oil and wax solution described above dispersed in a pharmaceutically acceptable carrier.

The treatment material of the invention comprises the solution formed from an oil and a wax that is sterile and pharmaceutically suitable for addition to the eye. The treatment composition comprises the solution dispersed in a carrier, preferably water, together with other treatment components such as a charged phospholipid, stabilizers, pH adjustors, etc. The treatment composition is applied to the ocular surface by topical application, by application to an optical prosthesis which is then inserted into the eye or by topical application to the eye containing an optical prosthesis. Whether applied directly to the eye or by application to a prosthesis, treatment is preferably by application of the oil and wax gel in a liquid vehicle. More preferably, the treatment composition is in the form of an aqueous, meta-stable colloid or emulsion where the gel comprises the dispersed (organic) phase.

The oil component used to form a gel may be derived from animals, plants, nuts, petroleum, etc. Oils derived from petroleum are usually aliphatic or aromatic hydrocarbons that are essentially free of polar substitution and are most preferred for purposes of the present invention provided the oil is refined so as to be compatible with human tissue such as the ocular surface. Preferably, the oil is a liquid hydrocarbon oil at room temperature having from 10 to 50 carbon atoms and more preferably, the oil is a saturated n-alkane or isoalkane hydrocarbon having from 14 to 26 carbon atoms. Unsaturated alkene hydrocarbons may be used but are less chemically stable as the double bonds tend to oxidize. Aromatic oils are lesser preferred because it is known that aromatic compounds are for the most part unsuitable for application to the ocular surface. Those oils derived from animals, plant seeds, and nuts are similar to fats and are primarily glycerides or fatty acids and consequently, contain a significant number of acid and/or ester groups rendering the same polar. Such oils are least preferred for purposes of the invention but may be used if used in concentrations not exceeding about 5 microliters of the oil.

The wax dissolved into the oil is a wax as typically used in cosmetics and may be of animal, vegetable or mineral origin or may be synthetically derived though mineral waxes are lesser preferred. Regardless of the origin of the wax, it should possess good film forming capability, be compatible with the oil and other components of the treatment composition in the concentration used, and be capable of dissolving into or gelling with the oil, be compatible with the ocular surface, preferably have a melting point between about 30° C. and 95° C. and more preferably between about 30° C. and 65° C. and most preferably, should be essentially free of triglycerides. A discussion of waxes and their properties can be found in the *Encyclopedia of Polymer Science and Engineering*, published by John Wiley and Sons, Volume 17, pp. 784–794, New York, 1989 and Kirk Othmer, *Encyclopedia of Chemical Technology*, 3rd edition, Volume 24, John Wiley and Sons, pp. 466–480, 1984, both incorporated herein by reference.

With respect to the above requirements for the wax, compatibility with the oil and other components of the formulation means that the wax component is capable of dissolving into or gelling with the oil in the concentration range in which it is used and otherwise, is chemically non-reactive with components of the treatment composition. Compatibility with the ocular surface means that the wax component of the treatment material is non-toxic and preferably does not cause stinging when administered to the ocular surface. The melting point limitation is to assure that the gel formed from the oil and wax is not unduly hard and is desirably liquid on the ocular surface of the eye (at body temperature). Otherwise, particulates might be present on the ocular surface that could cause blurring, a feeling of grittiness on the eye and discomfort. The freedom from triglycerides assists in film formation and the procedure to rid the wax of the triglycerides results in the in situ formation of dispersants that aid in dispersing the organic phase through an aqueous carrier.

Suitable waxes for purposes of the invention are esters of a long chain fatty alcohol and a long chain fatty acid having a chain length preferably within the range of from 12 to 50 carbon atoms. Examples of suitable waxes include carnauba wax, spermaceti wax, beeswax, bayberry (myrtyl) wax, candelilla wax, cetyl ester waxes such a ceryl certoate inclusive of Chinese wax, montan wax, cerbellina wax, etc. A preferred wax is beeswax. A lesser preferred wax is jojoba wax which is liquid at room temperature. In accordance with a preferred embodiment of the invention, the wax is treated to remove triglycerides using procedures to be described in greater detail below.

A generalized method for forming what is believed to be a solution or gel of the oil and wax is by blending the oil and wax together in a desired ratio. The mixture is then heated to a temperature above the melting point of the wax with stirring. A solution of the wax in the oil is obtained, that upon cooling, results in a composition that has the consistency of a gel of the two components. The gel formed may vary in hardness from a soft, viscous fluid to a hard material that appears to be solid dependent upon the ratio of oil to wax and the melting point of the wax. Larger concentrations of the wax, and/or higher melting point waxes form harder gels. Hence, the ratio of oil to wax and melting point of the wax must be controlled so as to form a gel capable of rapidly spreading over the ocular surface. In this respect, the weight ratio of the oil to the wax preferably varies between 200:1 and 5:1 and more preferably varies between 100:1 and 10:1.

If the gel is formed by the above procedure, it has been found that to form a sustained tear film over the eye, it is desirable if the gel is hydrated prior to addition to the eye. Hydration can be accomplished by wetting the gel with an aqueous solution, preferably containing a surfactant, for at least several hours before adding the same to the eye. Preferably, the gel is left in contact with the aqueous solution for a time sufficient for the particle to adsorb at least one quarter and preferably one-half of its weight in water.

In a preferred embodiment of the invention, where the gel is dispersed in an aqueous carrier, the gel is formed by separately adding the oil and wax to water and heating the aqueous dispersion so formed with stirring to an elevated temperature for an extended time. A preferred temperature is at least 50° C. and more preferably, from 75° to 90° C. Heating is continued for at least several minutes and more preferably for at least two hours. Further in accordance with the preferred embodiment of the invention, a base such as sodium or potassium hydroxide is added to the reaction mixture in an amount sufficient to raise the pH to between about 8 and 9 prior to the step of heating and to hydrolize from about 10 to 20 percent of the wax which amount represents the amount of triglycerides typically found in the wax. The hydrolysis of triglycerides present as impurities in either the wax or the oil converts the same to long chain fatty alcohols which assist in dispersing of the resultant gel throughout the aqueous medium. Following the reaction, the product is desirably neutralized to reduce the pH to between about 7.0 and 7.5 by addition of an acid such as hydrochloric acid. The removal of the triglycerides from the wax by alkali saponification substantially improves the ability of the composition to form a long lasting film over the eye.

The total amount of treatment material added to the eye preferably does not exceed 25 microliters (ul), more preferably varies between about 1 and 10 ul and most preferably varies between about 1 and 5 ul. In accordance with the subject invention, the total quantity of the gel added to the eye is desirably maintained within these concentration ranges. If the amount of gel on the ocular surface is in excess of 25 ul, and with most patients, in excess of 10 ul, the film formed on the surface of the eye may be too thick with formation of globules on the surface of the eye. This is likely to cause prolonged blurring. Consequently, to avoid blurring, the dose of the gel added to the eye most desirably does not exceed 10 ul though it should be understood that for some applications, such as application of medicaments to the ocular surface, larger doses may be desired notwithstanding that such doses may cause blurring.

The gel can be added directly to the eye. If the gel is added directly, recognizing that it is desirable to control dosage, a suitable method of application comprises placing a small quantity of the gel on a glass rod dispenser. The quantity of the gel preferably does not exceed the 10 ul dosage indicated above. The rod is then placed against the inside of the lower lid lining (conjunctiva) and rotated to transfer the gel to the eye. With blinking, the gel rapidly forms a film over the eye.

For self-administration of the gel of the invention to the eye, it is desirably admixed with a carrier and added to the eye in the form of a treatment composition, most preferably in the form of a colloid or emulsion of the gel in an aqueous carrier. Again, to avoid blurring, as described above, the total volume of gel available for formation of the tear film desirably does not exceed 25 ul and more preferably, does not exceed 10 ul.

It is known that the eye cannot accommodate a volume of more than about 10 ul of liquid. It is also known that excess liquid will be discharged or expressed from the eye during blinking immediately following addition of a liquid to the eye. Treatment composition added to the eye and discharged from the eye will carry treatment material with it. Consequently, following addition of a treatment composition to the eye, a portion of the efficacious component is immediately lost by blinking and discharge together with its liquid carrier. If a treatment composition added to the eye is in the form of a stable colloid or emulsion that differentiates slowly on the ocular surface, a volume of treatment material lost by discharge will be greater than the volume lost using a colloid or emulsion that rapidly differentiates on the ocular surface. For this reason, the treatment composition of the invention is preferably in the form of a meta-stable emulsion or colloid which is defined as a composition that is sufficiently stable to provide a uniform dose to the eye but is relatively unstable and rapidly differentiates upon contact with the eye, preferably differentiating within about 5 blinks following application of the composition to the eye or within about 30 seconds. A meta-stable emulsion or colloid is likely to separate on standing with formation of a layer containing agglomerated gel particles. An emulsion suitable for application to the eye is readily formed by shaking the treatment composition prior to administering the same to the eye to reform the meta-stable emulsion.

In view of the above, the total amount of a treatment composition containing the gel in a carrier added to the eye per treatment per eye preferably does not exceed 100 ul (about 2 drops) and more preferably varies between about 25 and 50 ul. This dose can be readily controlled and administered using a dispenser such as an eye dropper that permits addition of a single drop of treatment material to the eye.

Since it is desired to limit the total volume of treatment composition added to the eye while recognizing excess is discharged from the eye by blinking, and further recognizing that the total volume of treatment material available to form the tear film is desirably controlled so as not to exceed 25 ul, and preferably does not exceed 10 ul, it is apparent that the concentration of the gel in the treatment composition should be adjusted to provide the desired small dose of the gel while compensating for that lost due to discharge of excess treatment composition by blinking.

For reasons stated above, rapid differentiation of an emulsion and formation of the film over the corneal surface is desirable. The formation of the film is desirably assisted by use of a surfactant in the treatment composition which assists in spreading the gel over the eye. The surfactant should be one that enables rapid phase differentiation and further, should be one compatible with composition components and physiologically compatible with the eye—i.e., it should not be toxic nor cause stinging. Preferred surfactants are polyoxyethylene fatty acid ethers and esters. The surfactant is added to the composition in minor amount, preferably in an amount of less than 1.0 percent by weight and preferably within a range of from 1.10 to 0.35 percent by weight.

In a treatment composition, the gel may vary within reasonable limits provided the amount of gel retained on the eye is within the controlled volumes set forth above. A treatment composition containing the treatment material, the gel, in a concentration of at least 0.5 percent by weight of the total treatment composition provides some benefits. A preferred concentration for the gel is at least 1.0 percent of the weight of the total weight of the treatment composition. Preferably, the gel content of the treatment composition varies between about 2.5 and 12.5 percent by weight of the total treatment composition.

A phospholipid may be included in the treatment composition of the invention if desired. Suitable phospholipids are those carrying a net positive or negative charge under conditions of use. The preferred materials are those carrying a net negative charge because the negatively charged material will be repelled by the negatively charged ocular surface thereby permitting the maintenance of a relatively thick aqueous layer. The most preferred phospholipid is a polyol with a net negative charge, such as a phosphatidylglycerol or a phosphatidylinositol. The positively charged phospholipid is lesser preferred because it would be attracted to the negatively charged ocular surface thus compressing the tear film. Hence the positively charged phospholipids operate in a different manner than the negatively charged phospholipids and are lesser preferred. Suitable phospholipid additives are fully disclosed in the above-cited U.S. Pat. No. 4,914,088.

Other additives may be present in the treatment composition including minor amounts of neutral lipids and oils such as one or more triglycerides, cholesterol esters, and cholesterol; high molecular weight isoprenoids; stabilizers, surfactants; preservatives; pH adjusters to provide a composition preferably having a pH between about 5.0 and 8.5 and more preferably, between 6.0 and 7.4 and most preferably, between about 6.4 and 7.2; salt, glycerol or sugar in sufficient concentration to form an isotonic or mildly hypotonic composition; etc., all as would be obvious to those skilled in the art.

An especially useful class of additives are medicaments because the long-term stability of the film formed over the surface of the eye using the compositions of the invention results in improved delivery of the medicament to the eye due to increased contact time of the medicament with the eye. Medicaments suitable for delivery to the eye using the film forming compositions of the invention are those soluble in either the aqueous or oil phase of the composition. Illustrative medicaments include antibiotics, antiviral agents, anti-inflammatory agents, anti-fungal agents and anti-glaucoma agents such as illustrated in part in U.S. Pat. No. 4,522,803, Section 5.3.1 and 5.3.2, column incorporated herein by reference.

The treatment compositions of the invention are also desirably used with subjects requiring ocular prostheses. In this instance, the treatment composition enhances the tear film layer and lubricates the boundary between the prosthesis and the ocular surface. When used with an ocular prosthesis, the treatment composition may be applied to the inner or both the inner and outer surfaces of the prosthesis prior to insertion of the same into the eye. Alternatively, the treatment composition may be added directly to an eye in which an ocular prosthesis has previously been added. Regardless of how added, the amount available to form the oil layer should be within the limits set forth above.

Since the treatment compositions of the invention are to be added to the eye, the compositions should be sterile and should be packaged in sterile containers. Moreover, the treatment compositions must be pharmaceutically acceptable for addition to the eye. In this respect, they should be free of components incompatible with the ocular surface. For example, the treatment compositions should be free of solid particulates such as fillers, dyes, pigments and other components such as components that might cause stinging and irritation in contact with the ocular surface.

The invention will be better understood by reference to the examples which follow. In many of the examples that follow, a tear film is formed over an ocular surface by either adding one standard drop of treatment solution (40 to 50 ul) or by adding the gel directly to the eye by means of the glass rod. Thereafter, the tear film formed is evaluated by projecting a light source onto the ocular surface and viewing the reflected images from the light source on a video screen. The light source and its location is one that illuminates a surface area on the ocular surface of approximately 10 mm². Interference patterns are formed, the color(s) of which are indicative of the thickness of the oil layer over the ocular surface. The color of the waves is correlated with a protocol of known film thickness. In this way, tear film is evaluated over a period of real time and first rated in accordance with the following scale:

| Rating | Film Characteristics | Quality |
| --- | --- | --- |
| A | Colored waves - particularly greens and blues. Waves extend from lower lid to above the lower pupillary border. Film thickness is in excess of 170 nm. | Excellent |
| B | Colored waves - reds, browns, yellows, but no blues. Waves extend from lower lid to above the lower pupillary border. Film thickness of approximately 140 nm. | Very Good |
| C | Colored waves - only yellow is present. Waves extend from lower lid to lower pupillary border. Film thickness of approximately 90 nm. | Good |
| D | Waves visible but no color present or no color other than grayish white. Waves extend from lower lid to lower pupillary border. Film thickness of less than 55 nm. | Fair |
| F | No waves and no color. An absence of any observable tear film movement. Film thickness of less than 25 nm. | Poor |

With respect to the above categories, it should be recognized that because of the thin films evaluated for the D and F categories, the film thickness is a rough approximation.

Having rated the tear film as described above, a numerical format is then utilized to express change in tear film thickness. A numerical grade of 1.0 indicates a change of one letter grade—e.g., if a C baseline finding prior to the application of a drop of treatment composition improved the tear film to a B rating, a numerical grade of 1.0 would be given. A 2.0 numerical grade would indicate a two letter grade improvement; and a 3.0 numerical grade would indicate a three letter grade improvement. For many of the following examples: a 3.0 numerical grade represents an improvement from a D to an A, the maximum improvement in accordance with the testing method used because subjects with a grade of F were screened and eliminated from testing. In some of the examples, a rating in excess of 3.0 is given. In such instances, the films formed were exceptional and off scale.

In most examples, the evaluation of the tear films formed using the treatment composition was over a period of four hours to determine residence time of the film on the eye. Therefore, with time, the numerical rating decreases but in all cases, the numerical rating is based upon the baseline tear film prior to addition of the treatment composition.

EXAMPLES 1 TO 26

The following examples illustrate preparation of a gel in accordance with one embodiment of the invention and the physical appearance of the same following cooling. In all cases, gels of oil and wax were prepared by mixing the oil and wax together at a temperature above the melting point of the wax. In Examples 1 to 9, Drakeol 35 hydrocarbon oil was used, a hydrocarbon oil available from Penreco Corporation of Butler, Pa. In Examples 10 to 17, Drakeol 15 was used. The difference between the oils is molecular weight. The wax used was white bleached beeswax flakes in Examples 1 to 17, cetyl ester wax in Examples 18 to 20, carnauba wax in Examples 21 to 23 and jojoba wax in Examples 24 to 26. The following formulations were prepared.

| Example No. | Oil | Wt. % Wax | Gel Characteristics |
| --- | --- | --- | --- |
| Beeswax Formulations | | | |
| 1 | Drakeol 35 | 15.09 | Milky white soft solid that melts on body contact. |
| 2 | Drakeol 35 | 10.04 | Substantially the same as gel formed in Example 1. |
| 3 | Drakeol 35 | 5.02 | Softer, less white viscous liquid and has |

-continued

| Example No. | Oil | Wt. % Wax | Gel Characteristics |
|---|---|---|---|
| 4 | Drakeol 35 | 2.51 | oil-like feeling in hand. Shiney, very viscous liquid. |
| 5 | Drakeol 35 | 1.24 | Viscous liquid that will slowly flow when contaner is tipped. |
| 6 | Drakeol 35 | 0.62 | Almost completely transparent viscous liquid that flows as a liquid. |
| 7 | Drakeol 35 | 0.31 | Viscous liquid that flows readily |
| 8 | Drakeol 35 | 0.16 | Water white liquid having viscosity essentially of oil. |
| 9 | Drakeol 35 | 0.08 | Water white liquid having viscosity essentially of oil. |
| 10 | Drakeol 15 | 10.16 | Solid white material soft to the touch and capable of melting on hand. |
| 11 | Drakeol 15 | 5.14 | Essentially same as formulation of Example 10. |
| 12 | Drakeol 15 | 2.63 | Similar to formulation of Example 10 but less opaque and softer. |
| 13 | Drakeol 15 | 1.31 | Opaque, viscous liquid. |
| 14 | Drakeol 15 | 0.66 | Opaque viscous liquid but less opaque than Example 13. |
| 15 | Drakeol 15 | 0.33 | Thin liquid that remains opaque. |
| 16 | Drakeol 15 | 0.17 | Thin liquid somewhat opaque with viscosity essentially that of oil. |
| 17 | Drakeol 15 | 0.09 | Thin liquid somewhat opaque with viscosity essentially that of oil. |
| Cetyl Ester Wax Formulations | | | |
| 18 | Drakeol 15 | 15.16 | Cloudy vaseline-like liquid. |
| 19 | Drakeol 15 | 9.92 | Cloudy vaseline-like liquid somewhat less viscous than gel of Example 18. |
| 20 | Drakeol 15 | 4.98 | Mildly turbid viscous liquid. |
| Carnauba Wax Formulations | | | |
| 21 | Drakeol 15 | 14.98 | Yellow, hard waxy-like material. |
| 22 | Drakeol 15 | 10.16 | Similar to Example 21 but softer. |
| 23 | Drakeol 15 | 5.07 | Yellow cloudy vaseline-like material. |
| Jojoba Wax Formulations | | | |
| 24 | Drakeol 15 | 14.91 | Yellow, liquid material having viscosity essentially that of Drakeol. |
| 25 | Drakeol 15 | 9.66 | Same as for Example 24. |
| 26 | Drakeol 15 | 4.90 | Same as for Example 24. |

In all cases, the wax and oil were mixed together and heated to a temperature above the melting point of the wax, typically in excess of 70° C., and then cooled. The jojoba wax was liquid at room temperature and had a viscosity essentially equivalent to that of the oil and therefore, did not require heating.

Examples 27–36

In the following examples, a number of the gels were administered to the eye using a glass rod having a bulbous end and compared to neat Drakeol oil. In all examples, the treatment material was applied to the end of the glass rod and applied to the eye in a dose of from 3 to 10 microliters. It is believed that approximately equal amounts of treatment material were applied to the eye in each of the examples.

Example 27 represents the neat Drakeol oil. Examples 31, 34 and 35 exemplify the use of hydrated gels obtained by forming emulsions of the gel and permitting the emulsions to coagulate. The hydrated coagulant from the emulsions was then removed from its container on the end of a glass rod and applied to the eye. In these examples, the wax content of the hydrated gel was 0.5 percent of the total of the treatment material and the oil used was Drakeol 35. In Example 31, the wax was from beeswax, in Example 34, the wax was cetyl ester wax and in Example 35, the wax was carnauba wax.

For the remaining examples, selected gels from Examples 1 to 26 were used and the designation "Comp. of" in the following table refers to the examples. The designation "0" in the table under rating means immediately following instillation of the treatment material to the eye followed by about 30 seconds to permit film formation. The designation "nm" in the table means that for that data point, a measurement was not taken.

| Ex. No. | Comp. of | Rating After Time on Ocular Surface (hours) | | | | | | | |
|---|---|---|---|---|---|---|---|---|---|
| | | 0 | 0.5 | 1 | 2 | 3 | 4 | 5 | 6 |
| 27 | neat oil | 3.4 | 2.8 | 2.3 | 1.6 | 1.1 | 0.6 | 0.4 | 0.3 |
| 28 | 5 | 3.4 | 2.9 | 2.3 | 1.7 | 1.2 | 0.6 | 0.4 | 0.3 |
| 29 | 3 | 3.2 | 2.9 | 2.7 | 1.3 | 0.5 | nm | nm | nm |
| 30 | 1 | 3.2 | 3.0 | 2.7 | 13 | 0.6 | nm | nm | nm |
| 31 | — | 3.3 | 3.0 | 2.4 | 2.0 | 1.3 | 1.0 | 0.7 | 0.4 |
| 32 | 20 | 3.2 | 2.7 | 2.1 | 0.9 | 0.4 | 0.2 | 0.0 | — |
| 33 | 18 | 3.2 | 2.7 | 2.1 | 1.2 | 0.6 | 0.3 | 0.0 | — |
| 34 | — | 3.3 | 2.7 | 2.0 | 1.6 | 0.9 | 0.7 | 0.5 | 0.3 |
| 35 | — | 3.4 | 3.3 | 2.7 | 1.9 | 1.4 | 1.2 | nm | nm |
| 36 | 26 | 3.1 | 3.0 | 2.3 | 1.3 | 0.5 | 0.5 | 0.2 | nm |

The gel of the carnauba wax and oil (Example 35) is more dense than the gel formed using beeswax. Upon insertion of coagulant of the gel onto the ocular surface, an excellent tear film is formed, though a mild grittiness on the eye following instillation of the particle onto the eye is experienced by the subject. The gel of this example was difficult to disperse in an aqueous phase. As with the carnauba wax, the gel formed using cetyl ester wax (Example 34) was difficult to disperse in an aqueous phase.

EXAMPLES 37–41

In these examples, a treatment solution was made by dissolving a stabilizer and preservative as indicated and sodium chloride in water and adjusting pH and osmolarity. Thereafter, a surfactant is added and the solution is heated to a temperature of from 70° to 80° C. A gel is then made in a separate container using the procedures of Examples 1 to 26. The heated aqueous phase is then added to a homogenizer. While the homogenizer is running, the heated gel is added to the aqueous phase. Following addition of the gel, homogenization is continued for about two minutes and then the mixture is permitted to cool to room temperature with stirring. In the formulation chart below, the concentration of oil and wax is the concentration in the total of the treatment composition recognizing that the oil and wax are gelled prior to addition to admixture with the carrier.

| Formulation | |
|---|---|
| Component | Amount (% by Wt.) |
| Ethylenediaminetetraacetic acid | 0.10 |
| Sodium Chloride | to 250 m.o. |
| Alkane Oil | 10.00 |
| Surfactant | 0.19 |
| Beeswax | variable |
| Preservative | 0.10 |
| Water | to 1 liter |

In the above formulation, the alkane oil was Drakeol 35 as identified above, the surfactant was a polyoxyethylene sorbitan monooleate sold under the tradename Tween 80 used in the quantity indicated except for Example 37 where the concentration was 0.10 percent, the preservative was benzalkonium chloride, and the beeswax was as identified above.

In the following presentation of data, the baseline for comparison is treatment with an oil containing emulsion free of a wax (Example 37). The treatment composition for Example 37 was prepared in the same manner as those containing the gel except for the step of adding the wax and the formation of the gel. The following results were obtained upon instillation of a standard drop of treatment composition to the eye (40 to 50 ul):

| Ex. No. | Beeswax Content | Rating After Time on Ocular Surface (hours) | | | | | | |
|---|---|---|---|---|---|---|---|---|
| | | 0 | 0.5 | 1 | 2 | 3 | 4 | 5 | 6 |
| 37 | 0.00 | 3.0 | 1.4 | 0.6 | 1.1 | 0.0 | — | — | — |
| 38 | 0.10 | 3.0 | 1.9 | 1.1 | 0.6 | 0.2 | nm | 0.1 | — |
| 39 | 0.25 | 3.1 | 1.7 | 1.1 | 0.7 | 0.4 | 0.3 | 0.0 | — |
| 40 | 0.50 | 3.3 | 2.5 | 2.3 | 1.6 | 1.1 | 0.7 | 0.4 | 0.3 |
| 41 | 1.00 | 3.3 | 3.3 | 3.2 | 2.6 | 2.0 | 1.5 | 1.1 | 0.7 |

EXAMPLES 42 AND 43

These examples compare the film forming capability of treatment materials of the invention with wax alone and a commercially available ocular treatment material. The film forming capability is determined immediately following instillation of the material to the eye. For comparison purposes, the hydrated gel of Example 31 and emulsion of Example 41 are compared to (1) an emulsion having the formulation of Examples 41 from which the oil was omitted leaving only wax component of the gel (Example 42) and (2) a commercially available ointment identified as Lacri-Lube sold by Allergan Pharmaceutical, Inc. consisting of white petrolatum in an amount of 56.8% and mineral oil in an amount of 42.5% (Example 43). The hydrated gel of Example 31 was applied with the glass rod. The emulsion of Example 41 was applied as a standard drop. The wax in the emulsion (Example 42) was applied by removing a particle of the wax from the emulsion with a glass rod and applying the particle to the eye. Lacri-Lube was applied with the glass rod.

The following results were obtained.

Film Formation: For the composition of the invention (Examples 31 and 41), prior to blinking, a thickened fluid with small droplets could be seen. With one and then two blinks, the fluid spread with heavy color formation. The droplets disappeared within three of four blinks. By the fifth blink, a uniform, heavy film was present on the eye without particles or irregularities. For the wax (Example 42), the particle remained beneath the lower lid and a film did not form over the ocular surface. Upon application of Lacri-Lube ointment (Example 43), a heavy, irregular film or slick formed with large globules present after instillation of the formulation onto the eye. With one or two blinks, this film was slowly moved so that it covered 20 to 40% of the exposed portions of the eye and sclera. It did not substantially spread with further blinking though after approximately 10 minutes, the film had significantly thinned. Small droplets, uniformly present over the entire surface of the cornea, were still visible.

Blur: With the formulations of Examples 31 and 41, there was no blur following addition of the treatment composition. No blur was experienced following the addition of the wax as would be expected in the absence of film formation. Considerable blur was experienced following the addition of Lacri-Lube. The blur continued for over ten minutes.

EXAMPLE 44

Since jojoba wax is liquid at room temperature, it was added neat to the eye using the glass rod procedure. It was found that initially an excellent film formed but the film did not sustain itself for in excess of about 1 hour.

EXAMPLES 45 TO 48

The following examples illustrate the currently preferred embodiment of the invention and describe an alternative procedure for formation of a gel.

| Final Formulation | |
|---|---|
| Component | Amount (% by wt |
| Ethylenediaminetetraacetic acid | 0.10 |
| Alkane Oil | 4.75 |
| Surfactant | 0.19 |
| Beeswax | 0.25 |
| Boric Acid | 1.86 |
| Sodium Chloride | to 260 mo |
| Water | one liter |
| pH | to 7.5 |

In the above formulation, the alkane oil was Drakeol 21 as identified above, the surfactant was a polyoxyethylene sorbitan monooleate sold under the tradename Tween 80, the preservative was sorbic acid and the beeswax was as identified above. The procedure used to make the above formulation comprised the following steps:

The above formulation was made by preparing a first solution containing the EDTA, sodium chloride and boric acid dissolved in 875 ml of water. Sodium hydroxide was added to bring the pH of the solution to about 8.0. The solution was heated to 85° C. with constant stirring using a stir bar. The surfactant and beeswax were added to the solution while maintaining the solution at 85° C. In a separate vessel, the alkane oil was heated to 75° C. The first solution was then added to a homogenizer and the heated alkane oil was slowly added while homogenizing the mixture over a period of time of 2 minutes with the mixture held at 80° C. to form an emulsion. The emulsion was then removed from the homogenizer and permitted to cool to ambient temperature with constant stirring using a stir bar. The so prepared composition was then autoclaved for 30 minutes at a temperature of about 120° C. While held at elevated temperature, it is believed that the wax and oil formed a solution in each other and triglycerides were hydrolized. Thereafter, a solution identical to the first solution was prepared to which 1 percent by weight sorbic acid was added. This newly prepared solution was added to the autoclaved solution in an amount of 1 part sorbic acid solution per nine parts of the emulsion. The pH was then adjusted to 7.5 with hydrochloric acid and the volume was adjusted to 1 liter.

A second formulation was made identical to the first with the beeswax content increased to 0.5%.

The formulations so prepared were then evaluated using four groups of patients on two different days. The results are set forth as numerical averages for each group where group 1 comprised 4 patients, group 2 comprised 5 patients, group 3 comprised 4 patients and group 4 comprised 5 patients. The results are set forth below:

| Ex. No. | Beeswax Content | Rating After Time on Ocular Surface (hours) | | | | | | | |
|---|---|---|---|---|---|---|---|---|---|
| | | 0 | 0.5 | 1 | 2 | 3 | 4 | 5 | 6 | 7 |
| 45 | 0.25 | 3.1 | 2.5 | 1.6 | 1.1 | 0.6 | 0.5 | 0.4 | 0.1 | 0.3 |
| 46 | 0.25 | 2.4 | 2.5 | 1.9 | 1.6 | 1.6 | 1.5 | 0.6 | 0.4 | 0.2 |
| 47 | 0.50 | 2.7 | 2.4 | 1.6 | 1.3 | 1.3 | 1.2 | 1.0 | 0.6 | 1.0 |
| 48 | 0.50 | 2.4 | 2.5 | 2.1 | 1.6 | 1.6 | 1.6 | 1.4 | 1.4 | 1.3 |

We claim:

1. A pharmaceutically acceptable tear film over an ocular surface comprising a layer of a gel of oil and wax over said ocular surface where said gel is liquid at body temperature, said layer of a gel present in an amount sufficient to form a tear film over the ocular surface and below an amount that would result in significant prolonged blurring of vision.

2. The tear film of claim 1 where the gel comprises the product resulting from the mixture of oil and wax at a temperature above the melting point of the wax where the oil and wax are present in a weight ratio of from between 200:1 and 5:1.

3. The tear film of claim 2 where the gel is formed by heating the oil and wax together dispersed in an aqueous media, 4. The tear film of claim 3 where the gel is formed in the presence of a base at a pH of at least 8.0.

5. The tear film of claim 2 where the ratio varies between 100:1 and 10:1.

6. The tear film of claim 2 where the oil is a hydrocarbon oil.

7. The tear film of claim 2 where the oil is an alkane oil.

8. The tear film of claim 2 where the wax is a film forming wax having a melting point between about 35° and 95° that is compatible with an ocular surface and capable of forming a gel with the oil when heated to a temperature above the melting point of the wax and cooled.

9. The tear film of claim 8 where the wax is beeswax.

10. The tear film of claim 2 where the volume of gel over the ocular surface does not exceed 10 microliters.

11. The tear film of claim 2 having an optical prosthesis thereon.

12. The tear film of claim 11 where the prosthesis is a contact lens.

13. The tear film of claim 2 containing a medicament.

14. A method for treating an eye, said method comprising applying a pharmaceutically acceptable gel of oil and wax onto the wax surface of the eye where said gel is liquid at body temperature and capable of forming a thin, uniform film in contact with the ocular surface, said gel present in an amount sufficient to form a tear film over the ocular surface and below an amount that would result in significant prolonged blurring of vision.

15. The method of claim 14 where the gel is the product resulting from the admixture of oil and wax at a temperature above the melting point of the wax where the oil and wax are present in a weight ratio of from between 200:1 and 5:1.

16. The method of claim 15 where the gel is formed by heating the oil and wax together dispersed in an aqueous media.

17. The method of claim 16 where the gel is formed in the presence of a hydroxide in an amount sufficient to raise the pH to at least 8.0.

18. The method of claim 15 where the ratio varies between 100:1 and 10:1.

19. The method of claim 15 where the gel is sterile and free of ingredients pharmaceutically incompatible with the ocular surface, the oil is a hydrocarbon oil and the wax is a film forming wax having a melting point between about 35° and 95° C. that is compatible with an ocular surface and capable of forming a gel with the oil when heated to a temperature above the melting point of the wax and cooled.

20. The method of claim 19 where the oil is an alkane oil.

21. The method of claim 19 where the wax is beeswax essentially free of triglycerides.

22. The method of claim 19 where the volume of gel applied to the eye does not exceed about 25 microliters.

23. The method of claim 19 where the volume does not exceed a volume of from about 1 to 10 microliters.

24. The method of claim 19 where the gel is applied to an optical prosthesis and the optical prosthesis is inserted on the eye.

25. The method of claim 24 where the prosthesis is a contact lens.

26. The method of claim 19 where the gel contains a medicament.

27. The method of claim 19 where the gel is applied to the ocular surface in the form of an oil in water emulsion 28. The method of claim 27 where the emulsion is a meta-stable emulsion.

29. The method of claim 24 where the total dose of the emulsion added to the eye does not exceed about 100 microliters.

30. The method of claim 29 where the gel is present in the emulsion in a concentration of at least 0.5 percent by weight of the total weight of the emulsion.

31. The method of claim 30 where the gel is present in the emulsion in a concentration ranging between 2.5 and 15.0 percent by weight.

32. The method of claim 30 where the emulsion contains a medicament.

33. The method of claim 30 including a step of insertion of optical prosthesis into the eye following application of the emulsion to the eye.

34. The method of claim 33 where the prosthesis is a contact lens.

35. A pharmaceutically acceptable ocular treatment composition comprising an aqueous oil in water emulsion containing a gel of oil and wax where said gel is liquid at body temperature and capable of forming a thin, uniform film in contact with the ocular surface.

36. The composition of claim 35 where the gel is sterile and free of ingredients pharmaceutically incompatible with an ocular surface and is the product resulting from admixture of a hydrocarbon oil and a film forming wax having a melting point between about 35° and 95° C. that forms a gel with the oil when heated to a temperature above the melting point of the wax and cooled.

37. The composition of claim 36 where the wax and oil are heated together in the presence of a base.

38. The composition of claim 37 where the wax and oil are heated together dispersed in aqueous medium and the base is present in an amount sufficient to hydrolize essentially all triglycerides contained in the wax.

39. The composition of claim 36 where the oil and wax are present in a weight ratio of from between 200:1 and 5:1.

40. The composition of claim 39 where the ratio varies between 100:1 and 10:1.

41. The composition of claim 40 where the oil is an alkane oil.

42. The composition of claim 36 where the wax is beeswax.

43. The composition of claim 36 where the emulsion is a meta-stable emulsion.

44. The composition of claim 36 where the gel is present in the emulsion in a concentration of at least 0.5 percent by weight of the total weight of the emulsion.

45. The composition of claim 44 where the gel is present in the emulsion in a concentration ranging between 2.5 and 15.0 percent by weight.

46. The composition of claim 36 where the emulsion contains a medicament.

47. A method for making an emulsion, said method comprising the steps of heating a mixture of an oil and wax in a weight ratio of oil to wax between 200:1 and 5:1 to a temperature above the melting point of the wax in aqueous media to form an oil in water emulsion.

48. The method of claim 47 where the aqueous medium contains a base in an amount to raise the pH of the mixture to at least 8.0.

49. The method of claim 48 where the base and temperature are sufficient to hydrolize essentially all triglycerides.

50. The method of claim 47 where the ratio of oil to wax varies between about 100:1 and 10:1.

51. The method of claim 47 where the oil is a hydrocarbon oil.

52. The method of claim 47 where the emulsion is free of ingredients pharmaceutically incompatible with an ocular surface, the oil is an alkane oil and the wax has a melting point between about 35° C. and 95° C. and is a film forming wax capable of forming a gel with the oil when cooled from a temperature above the melting point of the wax.

53. The method of claim 47 where the wax is beeswax.

54. The method of claim 47 where the emulsion contains a medicament.

55. The method of claim 47 where the emulsion is homogenized to form a meta-stable emulsion.

56. The method of claim 47 where the gel is present in a concentration of at least 0.5 percent by weight of the total weight of the emulsion.

57. The method of claim 56 where the concentration of the gel ranges between 2.5 and 15.0 percent by weight.

58. The method of claim 47 including the step of packaging the emulsion in a sterile container.

59. The method of claim 14 wherein the method is for treatment of dry eye symptoms.

60. The method of claim 14 wherein the gel is applied to the eye as eye drops.

* * * * *